United States Patent [19]  [11] 3,992,428
Müller et al.  [45] Nov. 16, 1976

[54] PROCESS FOR PREPARING BIS-(TRIMETHYLSILYL-)UREA

[75] Inventors: Horst Müller, Emmerting; Ignaz Bauer; Edgar Schmidt; Rudolf Riedle, all of Burghausen, all of Germany

[73] Assignee: Wacker-Chemie GmbH, Munich, Germany

[22] Filed: Feb. 5, 1976

[21] Appl. No.: 655,333

[30] Foreign Application Priority Data
Feb. 24, 1975  Germany............................ 2507882

[52] U.S. Cl. .................. 260/448.2 E; 260/448.2 N
[51] Int. Cl.² ......................................... C07F 7/10
[58] Field of Search .............................. 260/448.2 E

[56] References Cited
UNITED STATES PATENTS

| | | | |
|---|---|---|---|
| 3,346,609 | 10/1967 | Klebe ....................... | 260/448.2 E X |
| 3,895,043 | 7/1975 | Wagner et al. ........... | 260/448.2 E X |

OTHER PUBLICATIONS
"Chemical Abstracts," 59, 1963, p. 3945g.

*Primary Examiner*—Paul F. Shaver

[57] ABSTRACT

An improved process for preparing bis-(trimethylsilyl-)urea which comprises reacting urea with hexamethyldisilazane in the presence of a catalytic amount of salts selected from the class consisting of ammonia, basic amine comounds and quaternary ammonium hydroxides.

7 Claims, No Drawings

PROCESS FOR PREPARING BIS-(TRIMETHYLSILYL-)UREA

This invention relates to a process for preparing bis-(trimethylsilyl-)urea and more particularily to an improved process for preparing bis-(trimethylsilyl-)urea.

It is generally known that bis-(trimethylsilyl-)urea can be prepared by reacting urea with hexamethyldisilazane. (Chemical Abstracts, Vol. 59, 1963, column 3945 g). It is believed that the reaction proceeds in accordance with the following equation

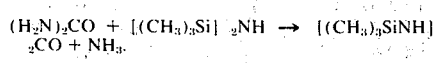
$$(H_2N)_2CO + [(CH_3)_3Si]_2NH \rightarrow [(CH_3)_3SiNH]_2CO + NH_3.$$

Since this reaction requires long reaction times at high temperatures, the resultant bis-(trimethylsilyl-)urea product is often contaminated with decomposition products such as trimethylsilylisocyanate.

Compared to processes known heretofore for the preparation of bis-(trimethylsilyl-)urea by reacting urea with hexamethyldisilazane, the process of this invention offers several advantages. For example, the reaction can be conducted at low temperatures and/or for shorter reaction times. Moreover, higher yields of bis-(trimethylsilyl-)urea which is substantially free of decomposition products, can be obtained, thereby resulting in greater amounts of hexamethyldisilazane being converted into the desired product.

Therefore, it is an object of this invention to provide an improved process for preparing bis-(trimethylsilyl-)urea. Another object of this invention is to provide a process for preparing bis-(trimethylsilyl-)urea at lower temperatures and/or for shorter reaction times. Still another object of this invention is to provide a process for preparing bis-(trimethylsilyl-)urea which is substantially free of decomposition products such as trimethylsilylisocyanate. A further object of this invention is to provide a process for preparing bis-(trimethylsilyl-)urea which will result in a greater conversion of hexamethyldisilazane into the desired product.

The foregoing objects and others which will become apparent from the following description are accomplished in accordance with this invention, generally speaking, by providing an improved process for preparing bis-(trimethylsilyl-)urea which comprises reacting urea with hexamethyldisilazane in the presence of a catalytic amount of salts selected from the group consisting of ammonia, basic amine compounds in which the active hydrogen is linked to the nitrogen atom (HN—bond) and the remaining valences of the nitrogen atom which are not saturated with hydrogen are saturated with carbon atoms and acid salts of quaternary ammonium hydroxides which in a dilute aqueous solution have an acid dissociation constant at 25° C. of at least $10^{-4}$.

Suitable examples of basic amine compounds which may be used in the preparation of the salts employed in this invention are n-butylamine, di-n-butylamine, tri-n-butylamine, sec.-butylamine, cyclohexylamine, guanidine, urea, o-aminoacetanilide, iminodiacetonitrile, m-aminoacetophenone, allylamine, N-methylallylamine, amylamine, N,N-dimethylamine, aniline, p-bromoaniline, 2,6-dinitroaniline, m-fluoroaniline, symm.-bis-(gamma-aminopropyl-)tetramethyldisiloxane, gamma-(N-aminoethylaminopropyl-)diphenylmethylsilane, o-iodoaniline, o-nitroaniline, 2,3,4,5-tetrachloroaniline, o-anisidine, 9-anthrylamine, 4,4'-diaminoazobenzyl, anthranilnitrile, benzylamine, p-methoxybenzylamine, the various decylamines, diallylamine, dicyclohexylamine, diethylenetriamine, difurfurylamine, di-m-tolylamine, beta-ethoxyethylamine, tetrahydrofurfurylamine, histamine, methylamine, morpholine, 5-nitronaphthylamine, 1,2-dimethyl-4-pentenylamine, N,N-diethyl-p-phenylenediamine, piperazine, piperidine, 2-aminopyridine, 6-nitro-o-toluidine, 2-amino-p-tolunitrile, 2-amino-p-tolunitrile, 9-phenanthrylamine, tribenzylamine, tri-n-propylamine, triisopropylamine and triethylamine.

The preferred basic amine compounds in which the active hydrogen is linked only to the nitrogen atom while the remaining valences of the nitrogen atom which are not saturated with hydrogen are saturated with carbon atoms are primary, secondary and tertiary amines corresponding to the general formula

$$R_aNH_{3-a},$$

wherein R which may be the same or different, represents hydrocarbon radicals such as alkyl, cycloalkyl, aryl and/or aralkyl radicals having up to 18 carbon atoms and a is a number of from 1 to 3, and urea.

The quaternary ammonium hydroxides may be represented by the general formula

$$NR_4OH.$$

where R is the same as above. Suitable examples of quaternary ammonium hydroxides are tetramethylammonium hydroxide, tetrabutylammonium hydroxide, benzyltrimethylammonium hydroxide and phenyltrimethylammonium hydroxide.

Examples of acids which have an acid dissociation constant of at least $10^{-4}$ in dilute aqueous solution at 25° C., i.e., a $pK_a$ value of at least 4, are perchloric acid, hydrochloric acid, hydrobromic acid, hydriodic acid, sulfuric acid, nitric acid, hydrofluoric acid, phosphoric acid, fluoroacetic acid, trichloroacetic acid, formic acid and p-toluenesulfonic acid as well as oxalic acid.

However, salts of the previously cited basic nitrogen compounds and acids which in a dilute aqueous solution have an acid dissociation constant of less than $10^{-4}$ such as acetic acid, carbonic acid, boric acid or sodium dihydrogen phosphate or alkylates of the cited basic nitrogen compounds such as benzyltrimethylammonium methylate are not suitable catalysts for effecting the reaction between urea and hexamethyldisilazane.

Because of their availability and because they result in the formation of effective salts, hydrochloric acid, sulfuric acid and p-toluenesulfonic acid are the preferred acids for the preparation of the salts employed in accordance with this invention.

The salts of ammonia, basic amine compounds in which the active hydrogen is linked only to the nitrogen atom while the remaining valences of the nitrogen atom which are not saturated with hydrogen are saturated with carbon atoms or acid salts of quaternary ammonium hydroxides which in a diluted aqueous solution at 25° C. have an acid dissociation constant of at least $10^{-4}$, can be prepared from mono or polybasic inorganic or organic acids. These salts can be neutral or acidic and they can be used alone or as mixtures to catalyze the reaction between urea and hexamethyldisilazane.

Examples of suitable salts which may be used as catalysts in this invention are ammonium chloride, ammonium sulfate, ammonium-p-toluenesulfonate, mono-n-butylammonium sulfate, guanidine hydrochloride, aniline hydrochloride, tetra-n-butylammonium chloride, ammonium trichloroacetate and ammonium oxalate.

The salts of ammonia, basic amine compounds or quaternary ammonium hydroxides having an acid dissociation constant of at least $10^{-4}$ in dilute aqueous solutions at 25° C. can be mixed with urea and hexamethyldisilazane as such or they can be prepared in situ by adding to the urea and hexamethyldisilazane an acid which in a diluted aqueous solution at 25° C. has an acid dissociation constant of at least $10^{-4}$ or by the addition of a compound from which such an acid can be derived, such as trimethylchlorosilane.

Generally the salts of ammonia, basic amine compounds in which the active hydrogen is linked to the nitrogen atom and the remaining nitrogen valences which are not saturated with hydrogen are saturated with carbon atoms or the acid salts of quaternary ammonium hydroxides having an acid dissociation constant of at least $10^{-4}$ at 25° C. in dilute aqueous solutions are employed in amounts of from 0.01 to 5 percent by weight and more preferably from 0.1 to 1 percent by weight based on the weight of the urea.

The urea, hexamethyldisilazane and the salt or an acid containing such salt and/or another compound from which such salt can be derived may be added to the reaction vessel in any desired sequence. Generally, the process can be carried out at temperatures between 40° and 225° C., but preferably the temperature range is from about 70° to 130° C. The process may be carried out at atmospheric pressure, subatmospheric or superatmospheric pressure, preferably at atmospheric pressure, i.e., at or near 760 mm Hg (abs.). The reaction should be conducted in the absence of water.

The hexamethyldisilazane and urea may be reacted in a stoichiometric amount, that is in a 1:1 mol ratio of hexamethyldisilazane to urea. However, an excess of hexamethyldisilazane may be employed, for example, up to about 300 percent in excess of stoichiometric amounts of hexamethyldisilazane may be used.

In order to achieve adequate mixing of the reaction components, it is preferred that the process of this invention be carried out in the presence of a solvent and/or in an excess of hexamethyldisilazane. Where the reaction is conducted in the absence of a solvent, then it is preferred that the amount of hexamethyldisilazane range from about 200 to 300 percent in excess of the stoichiometric quantity of hexamethyldisilazane.

Examples of solvents which may be used in the process of this invention are hydrocarbons such as benzene and toluene; esters such as ethyl acetate; ethers such as di-n-butylether, dioxane and tetrahydrofuran; ketones such as acetone; chlorinated hydrocarbons such as methylene chloride and siloxanes such as hexamethyldisiloxane.

Mixtures of various solvents may also be employed in the process of this invention. However, where a solvent is employed, then it is preferred that the amount of hexamethyldisilazane not exceed about 200 percent in excess of the stoichiometric amount required for the reaction. Excellent yields of bis-(trimethylsilyl-)urea are thus obtained with a minimum loss of hexamethyldisilazane.

Generally the reaction is complete when the evolution of ammonia has ceased. This generally requires from 50 to 150 minutes.

The yields of bis-(trimethylsilyl-)urea resulting from the process of this invention are at least 98 percent of theoretical.

In the following examples all parts are by weight unless otherwise specified.

EXAMPLE 1 a. A mixture containing 1500 parts by volume of hexamethyldisilazane, 180 parts of urea and 1 part of ammonium sulfate is heated to reflux temperature (approx. 125° C.). The evolution of ammonia is detected at about 80° C. After refluxing for about 1.25 hours the formation of ammonia has terminated. The reaction product is cooled, filtered and the filtered residue is dried at 12 mm Hg (abs.). About 603 parts (98.5 percent of theoretical) of bis-(trimethylsilyl-)urea having a purity of over 99 percent by weight are recovered.

b. For purposes of comparison, the process described in paragraph (a) above is repeated except that the reaction is conducted in the absence of ammonium sulfate. In this case ammonia is not evolved until the reaction temperature reaches about 125° C. and even after 12 hours the reaction is not complete.

c. In another comparison, the process described in paragraph (a) above is repeated except that 1 part NaNH$_4$HPO$_4$ is substituted for the ammonium sulfate. No reaction is observed.

d. In still another comparison, the process described in paragraph (a) above is repeated except that 1 part of benzyltrimethylammonium ethylate is substituted for the ammonium sulfate. Again, no reaction is observed.

EXAMPLE 2 a. A mixture containing 750 parts by volume of hexamethyldisilazane, 750 parts by volume of toluene, 180 parts urea and 0.5 part of ammonium chloride is heated to reflux temperature (approx. 110° C.). After refluxing for 1.25 hours the evolution of ammonia has stopped and the reaction is considered to be complete. The product is cooled, filtered and the filtered residue dried at 12 mm Hg (abs.). Approximately 603 parts (98.4 percent of theoretical) of bis-(trimethylsilyl-)urea having a purity in excess of 99 percent by weight are obtained.

b. For purposes of comparison, the process described in Example 2(a) is repeated except that the reaction is conducted in the absence of ammonium chloride. No reaction is observed.

EXAMPLE 3

Several mixtures, each of which contain 1500 parts by volume of hexamethyldisilazane, 180 parts of urea and the salts listed in Table 1 are heated to reflux temperature. The time required for one-half of the theoretical amount of ammonia to be formed is determined and the results are illustrated in the Table as "half-time value".

TABLE 1

| Salt | Amount, Parts | Half-time value, minutes |
|---|---|---|
| NH$_4$Cl | 0.5 | 42 |
| (NH$_4$)$_2$SO$_4$ | 0.5 | 42 |
| (NH$_4$)$_2$SO$_4$ | 1.0 | 23 |
| [N(n-C$_4$H$_9$)H$_3$]$_2$SO$_4$ | 0.5 | 41 |

TABLE 1-continued

| Salt | Amount, Parts | Half-time value, minutes |
|---|---|---|
| $NH_4O_3SC_6H_5CH_3$ | 0.5 | 25 |
| $HN=C(NH_2)_2 \cdot HCl$ | 0.5 | 73 |
| $C_6H_5NH_2 \cdot HCl$ | 0.5 | 80 |
| $N(n-C_4H_9)Cl$ | 0.5 | 125 |
| $NH_4OOCCCl_3$ | 1.0 | 92 |
| Comparison tests | — | 340 |
| $NH_4OOCCH_3$ | 1.0 | 155 |

EXAMPLE 4

Mixtures, each containing 750 parts by volume of hexamethyldisilazane, 180 parts of urea, 750 parts by volume of solvents and the salts listed in Table II are heated to reflux temperature. The time required in minutes for the development of one half of the theoretical amount of ammonia is illustrated as the "half-time value" in the Table.

TABLE II

| Salt | Amount, parts | Solvent | Half-time value, minutes |
|---|---|---|---|
| $NH_4Cl$ | 0.5 | toluene | 27 |
| $NH_4Cl$ | 1.0 | toluene | 20 |
| $NH_4Cl$ | 0.5 | $CH_3COOC_2H_5$ | 20 |
| $(NH_4)_2SO_4$ | 0.5 | $CH_3COOC_2H_5$ | 60 |
| $(NH_4)_2SO_4$ | 1.0 | toluene | 33 |
| $(NH_4)_2SO_4$ | 1.0 | acetone | 30 |
| $(NH_4)_2SO_4$ | 1.0 | $(CH_3)_3SiOSi(CH_3)_3$ | 90 |
| Comparison examples | | toluene | No $NH_3$ formed |
| — | — | $(CH_3)_3SiOSi(CH_3)_3$ | No $NH_3$ formed |
| — | — | $CH_3COOC_2H_5$ | very slow $NH_3$ development |

Although specific examples of the invention have been described herein, the invention is not to be limited solely thereto, but to include all the variations and modifications falling within the spirit and scope of the claims.

What is claimed is:

1. An improved process for the preparation of bis-(trimethylsilyl-)urea by reacting urea with hexamethyldisilazane, the improvement which comprises conducting the reaction in the presence of a salt selected from the class consisting of ammonium salts, salts of basic amine compounds in which an active hydrogen is linked to the nitrogen as an HN-bond and the remaining valences of the nitrogen atom which are not saturated with hydrogen are saturated with carbon atoms, and acid salts of quaternary ammonium hydroxides which in a dilute aqueous solution have an acid dissociation constant of at least $10^{-4}$ at 25° C.

2. The improved process of claim 1 in which the salt is present in an amount of from 0.1 to 5 precent by weight based on the weight of the urea.

3. The improved process of claim 1 in which the salt is an ammonium salt.

4. The improved process of claim 1 in which the salt is a salt of a basic amine compound in which an active hydrogen is linked to the nitrogen as an HN—bond and the remaining valences of the nitrogen atom which are not saturated with hydrogen are saturated with carbon atoms.

5. The improved process of claim 1 wherein the salt is an acid salt of a quaternary ammonium hydroxide.

6. The process of claim 1 wherein the reaction is conducted at a temperature of from about 40° to 225° C.

7. The process of claim 1 wherein the salt is produced in situ.

* * * * *